United States Patent [19]
Carson

[11] Patent Number: 5,976,388
[45] Date of Patent: Nov. 2, 1999

[54] METHOD AND APPARATUS FOR AUTOLOGOUS BLOOD SALVAGE

[75] Inventor: Gary Allen Carson, Golden, Colo.

[73] Assignee: Cobe Cardiovascular Operating Co., Inc., Arvada, Colo.

[21] Appl. No.: 08/859,645

[22] Filed: May 20, 1997

[51] Int. Cl.⁶ .................................................. B01D 21/26
[52] U.S. Cl. ......................... 210/782; 210/194; 210/252; 210/258; 210/360.1; 210/369; 210/379; 210/382; 210/787; 210/789; 210/805; 210/806; 494/36; 494/37; 494/67
[58] Field of Search ...................................... 210/739, 744, 210/782, 787, 789, 805, 194, 252, 258, 360.1, 364, 369, 378, 806, 379, 381, 382; 494/3, 10, 36, 41, 37, 67, 80; 604/4, 5, 6, 67; 435/2

[56] References Cited

U.S. PATENT DOCUMENTS

| | | |
|---|---|---|
| 868,288 | 10/1907 | Nilsson et al. ............................ 494/36 |
| 1,002,471 | 9/1911 | Thelitz ...................................... 494/36 |
| 1,355,559 | 10/1920 | Mauss ....................................... 494/36 |
| 3,409,213 | 11/1968 | Latham, Jr. . |
| 3,411,450 | 11/1968 | Clifton . |
| 3,470,824 | 10/1969 | O'Connor . |
| 3,487,784 | 1/1970 | Rafferty et al. . |
| 3,647,324 | 3/1972 | Rafferty et al. . |
| 3,655,123 | 4/1972 | Judson et al. ............................ 494/41 |
| 3,785,549 | 1/1974 | Latham, Jr. . |
| 3,957,389 | 5/1976 | Rafferty et al. . |
| 3,970,408 | 7/1976 | Rafferty et al. . |
| 4,037,984 | 7/1977 | Rafferty et al. . |
| 4,059,108 | 11/1977 | Latham, Jr. . |
| 4,086,924 | 5/1978 | Latham, Jr. . |
| 4,135,253 | 1/1979 | Reich et al. . |
| 4,185,617 | 1/1980 | Hutchins . |
| 4,257,744 | 3/1981 | Watson . |
| 4,300,717 | 11/1981 | Latham, Jr. . |
| 4,304,532 | 12/1981 | McCoy . |
| 4,380,416 | 4/1983 | Menager . |
| 4,408,952 | 10/1983 | Schweinfurter . |
| 4,464,167 | 8/1984 | Schoendorfer et al. ...................... 604/6 |
| 4,589,822 | 5/1986 | Clausen et al. . |
| 4,606,698 | 8/1986 | Clausen et al. . |
| 4,643,641 | 2/1987 | Clausen et al. . |
| 4,668,214 | 5/1987 | Reeder ...................................... 494/37 |
| 4,675,117 | 6/1987 | Neumann et al. ....................... 210/789 |
| 4,678,409 | 7/1987 | Kurokawa . |
| 4,688,998 | 8/1987 | Olsen et al. . |
| 4,722,661 | 2/1988 | Mizuno . |

(List continued on next page.)

FOREIGN PATENT DOCUMENTS

| | | |
|---|---|---|
| 0 619 145 A2 | 3/1994 | European Pat. Off. . |
| 0 664 159 A1 | 7/1995 | European Pat. Off. . |
| WO 93/20860 | 10/1993 | WIPO . |

OTHER PUBLICATIONS

COBE Laboratories, Inc., "COBE BRAT 2 Operator's Manual"(undated).

Haemonetics Corporation, "Cell Saver HaemoLite 2 Autologous Blood Recovery System Owner's Operating and Maintenance Manual," Apr. 1989.

*Primary Examiner*—John Kim
*Attorney, Agent, or Firm*—Popovich & Wiles, P.A.

[57] ABSTRACT

An improved autologous blood salvage system is provided in which blood is removed from a patient and may be processed in a manner wherein an anticoagulant solution is for cycled for reuse. Further, the system may be employed for contemporaneous blood filtering and red blood separation. In one embodiment, anticoagulated blood is contemporaneously filtered and defoamed within a rotating processing bowl, while red blood cells are separated, washed and collected within the bowl and an anticoagulant solution is cycled from the bowl for re-use. During a red blood cell removal mode, the flow of anticoagulated blood into the bowl may be suspended/terminated and the bowl pressurized to remove the red blood cells. The improved system provides for the recovery of a high quality red blood cell product, with reduced processing time requirements/user training, and reduced disposable componentry and related costs.

26 Claims, 5 Drawing Sheets

U.S. PATENT DOCUMENTS

| | | |
|---|---|---|
| 4,898,518 | 2/1990 | Hubbard et al. . |
| 4,943,273 | 7/1990 | Pages .......................................... 494/41 |
| 4,983,158 | 1/1991 | Headley ..................................... 494/41 |
| 4,984,972 | 1/1991 | Clausen et al. . |
| 5,021,048 | 6/1991 | Buckholtz ............................... 604/151 |
| 5,141,486 | 8/1992 | Antwiler ..................................... 494/37 |
| 5,147,186 | 9/1992 | Buckholtz . |
| 5,405,308 | 4/1995 | Headley et al. ........................... 494/67 |
| 5,427,695 | 6/1995 | Brown ...................................... 210/782 |
| 5,494,592 | 2/1996 | Latham, Jr. et al. .................... 210/782 |
| 5,651,766 | 7/1997 | Kingsley et al. ........................... 604/6 |

METHOD AND APPARATUS FOR AUTOLOGOUS BLOOD SALVAGE

FIELD OF THE INVENTION

The present invention relates to extracorporeal blood processing, and more particularly, to a method and apparatus for autologous blood salvage.

BACKGROUND OF THE INVENTION

The collection and reinfusion of a patient's own blood, referred to as autologous blood, offers a number of recognized benefits. For example, the use of autologous blood reduces concerns relating to the possibility of disease transmission via donor blood transfusions, referred to as homologous blood, as well as concerns regarding febrile/allergic reactions. Additionally, autologous blood recovery ensures the rapid availability of blood and reduces or eliminates the need for compatibility testing on such blood since the procedure is most typically completed in an operating room. Further, the use of autologous blood provides red blood cells which are generally superior in quality to banked blood and reduces any quantity of homologous blood otherwise needed. The use of autologous blood is also desirous to many patients for psychological and/or religious reasons.

Intraoperative procedures where autologous blood salvage is currently employed include cardiac and vascular surgery. Specialties which employ autologous blood salvage include orthopedics, plastic and reconstructive surgery, neurosurgery, solid organ transplants, general surgery, gynecology and trauma.

In a typical blood salvage procedure, blood is removed from or about a surgical site via a hand-held suction device, mixed with an anticoagulant, and transferred to a reservoir for subsequent transfer for batch processing. In connection with such collection/transfer of salvaged blood, the blood is typically filtered to remove debris and defoamed to remove entrained gaseous components (e.g. air) utilizing separate in-line filter devices and defoaming devices through which the salvaged blood is sequentially transferred. During batch processing, the salvaged blood and a wash solution are separately pumped in sequence through a centrifuge to separate red blood cells and achieve a degree of washing. Following processing, the red blood cells are removed from the centrifuge for reinfusion to the patient.

As can be appreciated, in completing a blood salvage operation, it is desirable to utilize an amount of anticoagulant that is sufficient to adequately address clotting to avoid line blockage and to further allow for maximum recovery of red blood cells. On the other hand, too much anticoagulant may result in not only waste and added fluid storage components, but additionally may result in unused anticoagulant being contained with the collected red blood cells, thereby compromising hemostasis upon reinfusion. Of further note, even when an appropriate amount of anticoagulant is utilized, the anticoagulant needs to achieve adequate mixing with the salvaged blood in order to achieve the desired relative concentration. To address this consideration, heparin is often employed since it diffuses quickly and is quite effective in preventing clots in low concentrations. Heparin may cause a number of adverse side effects, however, including, for example, post-operative bleeding from unneutralized heparin rebound, platelet activation, and allergenic reaction. Consequently, an acid citrate dextrose (ACD) anticoagulant may be preferred in many instances. ACD exhibits mixing difficulties, however, and is quite sensitive in relation to achieving the desired anticoagulant/blood ratio.

As to filtration, the desired capability to remove small debris must be balanced in relation to any potential filter plugging implications. That is, as filter pore sizing is decreased, the potential for filter plugging is increased. Such filter plugging presents particular design challenges where, for example, available filtration surface area is limited. Consequently, many blood salvage processes currently employ filters having 120 $\mu$ openings as opposed to a finer 40 $\mu$ opening since significant plugging would occur if 40 $\mu$ filters were employed.

With regard to the filtration, defoaming and blood processing steps in typical blood salvage procedures, the primary objectives are to obtain a high quality and amount of collected red blood cells in the least amount of overall procedure time. In this regard, the above-described separate filtration, and defoaming and steps, the separate red blood cell separation and wash steps on a batch basis, present significant tradeoff limitations between achieving a high-quality blood product and reducing overall procedure time requirements.

SUMMARY OF THE INVENTION

In view of the foregoing, an objective of the present invention is to provide an autologous blood salvage system yielding a high-quality blood product having high hematocrit, low contaminants and predictable anticoagulant level. In this regard, a specific objective is to provide a blood salvage system which allows for the reliable use of an acid citrate dextrose (ACD) anticoagulant or citrate phosphate dextrose (CPD) anticoagulant. An additional related object is to provide an autologous blood salvage system that yields a blood product that has been microfiltered (e.g. by filter media having 40 $\mu$ or smaller openings).

A further objective of the present invention is to provide an autologous blood salvage system that not only yields a high quality blood product, but also realizes high throughput and entails reduced operator training.

Yet another objective of the present invention is to reduce the number of components and related cost of disposables utilized, and to otherwise reduce the capital equipment costs necessary to achieve effective autologous blood salvage.

One or more of these objectives and additional advantages are realized by a system in which an anticoagulant, preferably in a solution, is introduced into blood removed from a patient to achieve at least a degree of anticoagulation. The anticoagulant blood mixture is then flowed into a containment area which is rotated about a rotational axis to create a centrifugal force pressure gradient within an annular fluid bed comprising the anticoagulant/blood mixture that accumulates within the rotating containment area. Such centrifugal force pressure gradient is utilized to separate red blood cells (RBCs) into an outer layer of the annular fluid bed within the containment area.

In one aspect of the present invention, an anticoagulant-containing mixture (e.g. anticoagulant and blood waste components) accumulating within the containment area is cycled from the containment area into a first reservoir for reuse (i.e., via reintroduction into blood removed from the patient). In this regard, the anticoagulant-containing mixture may be removed from the containment area utilizing the centrifugal force pressure gradient to force the anticoagulant centripetally towards the rotational axis then longitudinally out of the containment area to the first reservoir for reuse.

In a related aspect of the present invention, an anticoagulant is continuously introduced from the first reservoir into a transfer line utilized for patient blood removal during blood processing and directly flowed with any removed blood into the containment area for contemporaneous RBC separation and anticoagulant cycling for reuse. By virtue of the continuous "closed-loop" flow of anticoagulant in the system during blood processing, a desired anticoagulant-to-blood volume ratio can be achieved with enhanced mixing. Such advantages, in turn, allow an ACD or CPD anticoagulant to be effectively utilized. Additionally, by providing for the direct flow of removed blood and an anticoagulant to the containment area and contemporaneous processing/cycling thereof, blood processing can be achieved with reduced time requirements.

Relatedly, the present invention may utilize a premixed anticoagulant/wash solution (e.g. an ACD or CPD anticoagulant in a saline wash fluid) that is provided in the first reservoir. The use of a premixed anticoagulant/wash solution allows the anticoagulant wash solution flow rate to be set relatively high relative to and even exceed the flow rate of the removed blood, thereby enhancing mixing and further facilitating use of an ACD or CPD anticoagulant. That is, since the volume of anticoagulant wash solution is high relative to that of the removed blood, the concentration of anticoagulant will not vary significantly during operations, thus enhancing effective use of ACD or CPD. Further, by mixing the anticoagulant wash solution with the removed blood prior to separating and concentrating the red blood cells and contaminants in the containment area, removal of contaminants is more effective. In this regard, it is noted that once red blood cells and contaminants are concentrated in known devices, wash solution cannot uniformly or completely permeate the packed bed of cells. Additionally, use of a premixed anticoagulant/wash solution in the present invention provides for contemporaneous red blood cell separation and washing in the containment area during blood processing. The first reservoir may be of a predetermined volume which is greater than the premixed anticoagulant/wash solution volume, so as to accommodate the receipt and disposal of blood waste components that will be cycled from the containment area with the anticoagulant/wash solution during blood processing.

In yet another aspect of the present invention, the anticoagulant/blood mixture flowing into the containment area for processing may be advantageously filtered in the containment area to remove debris. In this regard, the centrifugal forces resulting from the rotation of the containment area can be utilized to flow the anticoagulant blood mixture through an annular filter media into a region of the containment area within which the blood is further anticoagulated, and red blood cells are washed by the anticoagulant/wash solution and separated utilizing the above-noted centrifugal force pressure gradient. As will be appreciated, filtering in the rotating containment area allows for contaminants to spin to and accumulate adjacent to an outer wall defining the containment area. As a result, the contaminants will not readily tend to "coat out" a large filter surface area with only a small volume of contaminants. This allows a given area of filter to handle a relatively large volume of debris. Further, by filtering within the containment area, a filter may be employed which presents a relatively large filtering surface area. In view of the noted advantages, the invention accommodates the micro-filtering of debris utilizing openings of 40 μ or less.

In one embodiment, an annular filter may be located in a bottom region of the containment area immediately above an annular, cup-shaped region for collecting and segregating the filtered debris. An annular defoaming member may also be positioned in the containment area above the filter to contact and thereby burst bubbles within the anticoagulant/removed blood mixture. In this regard, the centrifugal force pressure gradient may be employed to separate the gas bubbles toward the inner surface of the above-noted fluid bed, whereupon the gas bubbles contact the defoaming member and the released gas is removed from the containment area.

In an additional aspect of the present invention the flow of removed blood and anticoagulant into the containment area for blood processing may be suspended when a predetermined amount of red blood cells have been collected within the containment area. Upon such suspension, rotation of the containment area may be correspondingly suspended and the red blood cells may be removed from the containment area by pressurizing the containment area to force the collected red blood cells therefrom. In this regard, a baffle plate may be positioned above the noted annular filter, wherein the collected red blood cells will be directed by the baffle plate over the annular, cup-shaped region containing the filtered debris for removal. The collected red blood cells may be removed from the containment area utilizing the same access tube through which the removed blood/anticoagulant mixture is introduced, then selectively directed into a red blood cell collection reservoir for subsequent reinfusion to the patient.

DETAILED DESCRIPTION

An embodiment of an autologous blood salvage system 10 is illustrated in FIGS. 1–4 and includes a fluid transfer/storage assembly 50, a bowl/stator assembly 20, a bowl rotation motor 92, a vacuum/pressurization pump 94 and a user interface/control assembly 100. The fluid transfer/storage assembly 20 and bowl/stator assembly 50 may be provided in an interconnected, prepackaged form for use and disposal on a per-patient basis. In this regard, the present invention provides for such a disposable having reduced components and enhanced utility since separate storage/filtration/defoaming reservoirs are not needed, as per current systems.

Figure 1:
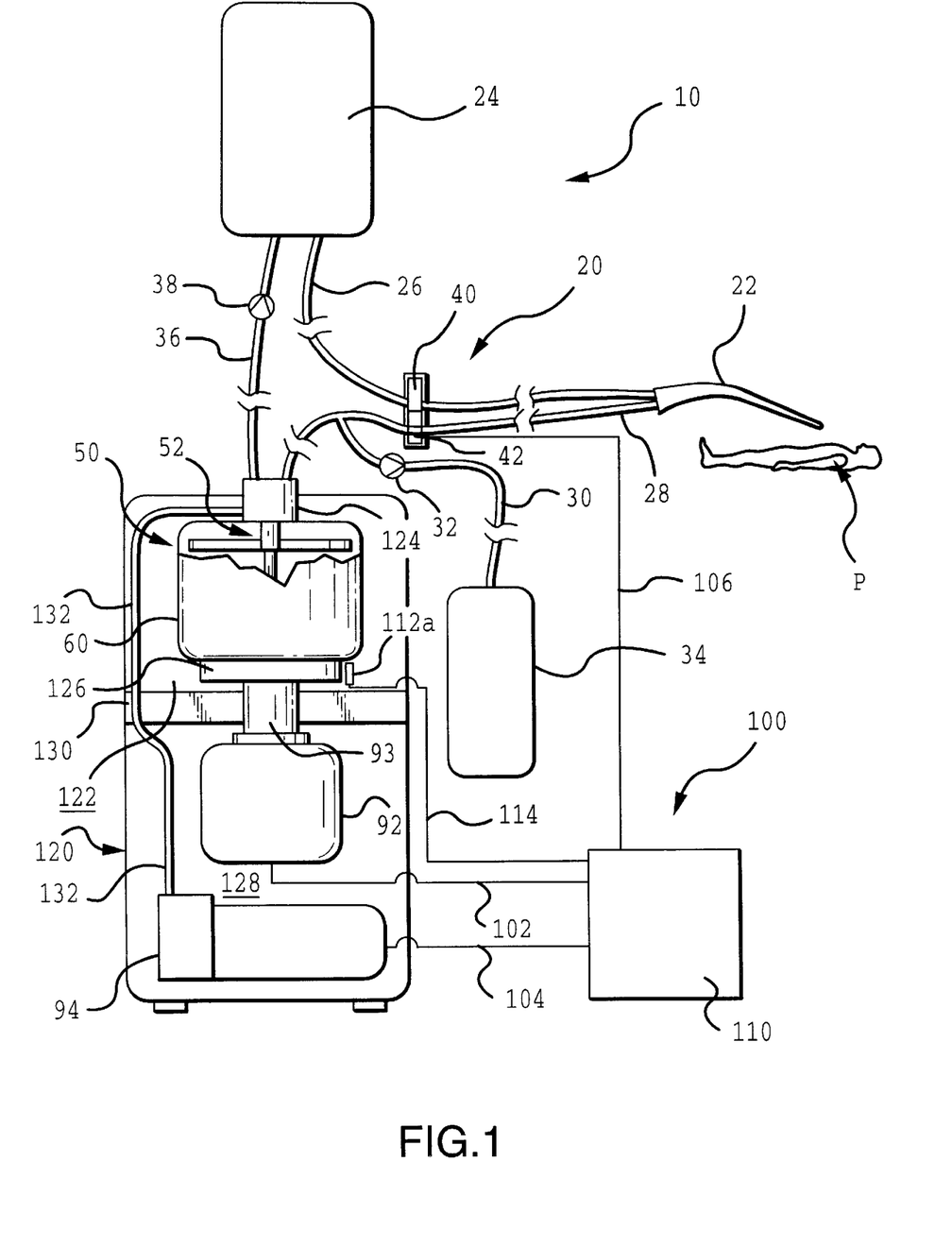
FIG. 1 is a schematic illustration of an autologous blood salvage system embodiment of the present invention.

In general, vacuum/pressurization pump 94 is utilized to draw a vacuum in bowl/stator assembly 50 and suction blood from the patient P via interconnected fluid transfer/storage assembly 20 into bowl/stator assembly 50 for blood processing. Motor 92 is utilized to rotate a cylindrical, containment bowl 60 about a stationary stator assembly 52 to process the blood and continuously cycle an anticoagulant/wash solution for reuse during a blood processing mode. Vacuum/pressurization pump 94 is further employed to pressurize the bowl 60 for removal of collected red blood cells following blood processing. User interface/control assembly 100 provides automated and/or selective user control over the operation of vacuum/pressurization when pump 94, motor 92 and other system components, as will be noted.

The fluid transfer/storage assembly 20 comprises a suction device 22 for hand-held use in selectively suctioning blood from a patient P in conjunction with an intraoperative procedure. Suction device 22 is interconnected to an anticoagulant/wash solution reservoir 24 via transfer tubing 26, and to bowl/stator assembly 50 via transfer tubing 28, wherein during blood processing anticoagulant/wash solution continuously flows into suction device 22 and transfer tubing 28, to anticoagulate blood as it is removed from a patient using suction device 22. Transfer/reservoir assembly 20 further includes a transfer tubing spur 30 having a check valve 32 (i.e., for one-way fluid transfer) for transferring red blood cells from containment bowl/stator assembly 50 to transfer bag 34 during a red blood cell removal mode following blood processing. Transfer tubing 36 with check valve 38 (i.e., for one-way fluid transfer) is also provided to transfer anticoagulant/wash solution with blood waste components from bowl/stator assembly 50 back to the anticoagulant/wash solution reservoir 24 for reuse during blood processing. Clamps 40 and 42 are provided for selectively suspending or terminating the flow of anticoagulant/wash solution and blood, respectively, through transfer tubing lines 26 and 28, respectively, during the red blood cell removal mode.

Figure 2:
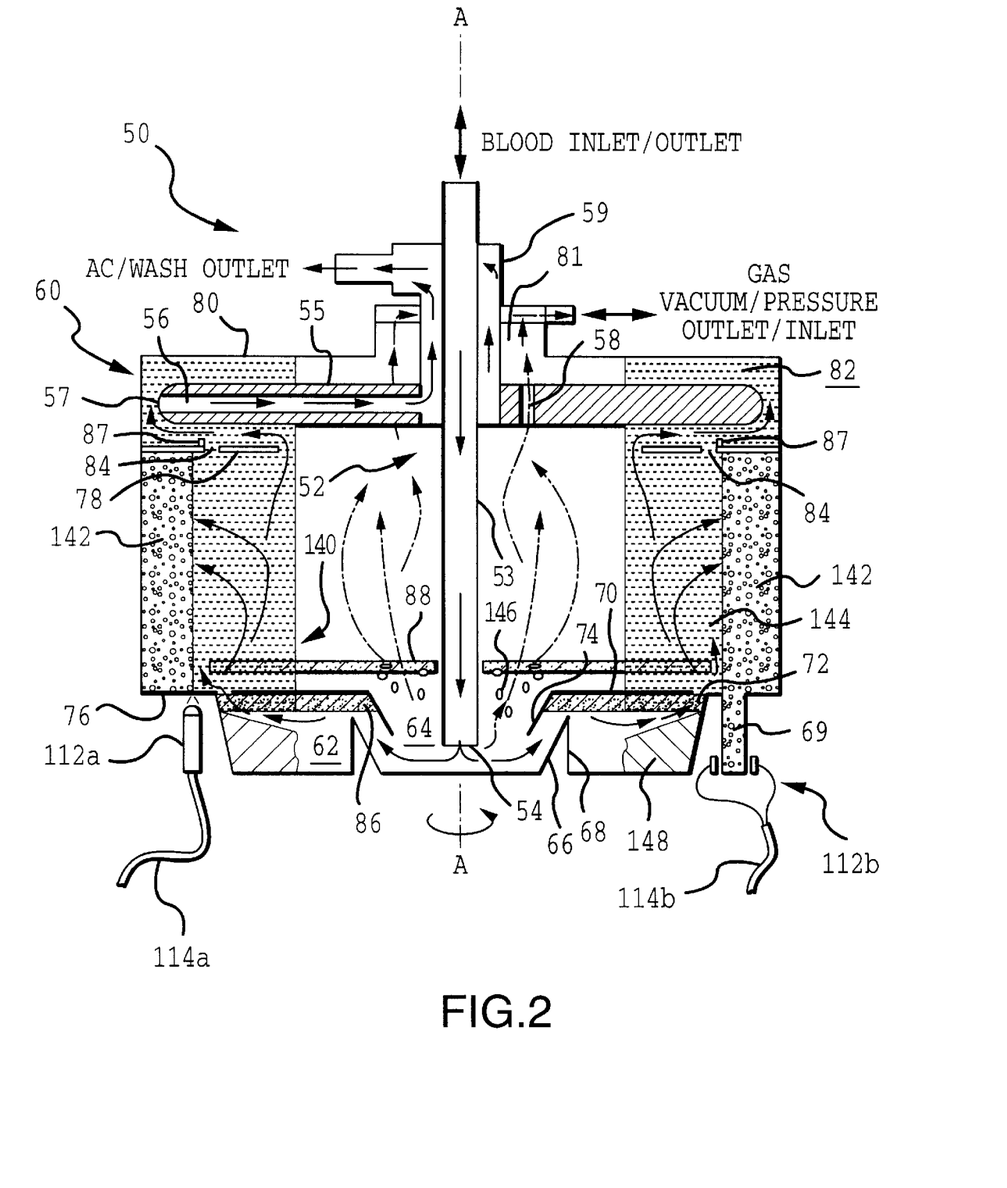
FIG. 2 is a cross-sectional side view of a containment bowl of the embodiment of FIG. 1 in a blood processing mode, wherein anticoagulated blood is processed in the rotating bowl to contemporaneously filter, defoam and further anticoagulate the blood; wash, separate and collect red blood cells from the blood; and centripetally pump anticoagulant/wash solution from the bowl for reuse.
Figure 3:
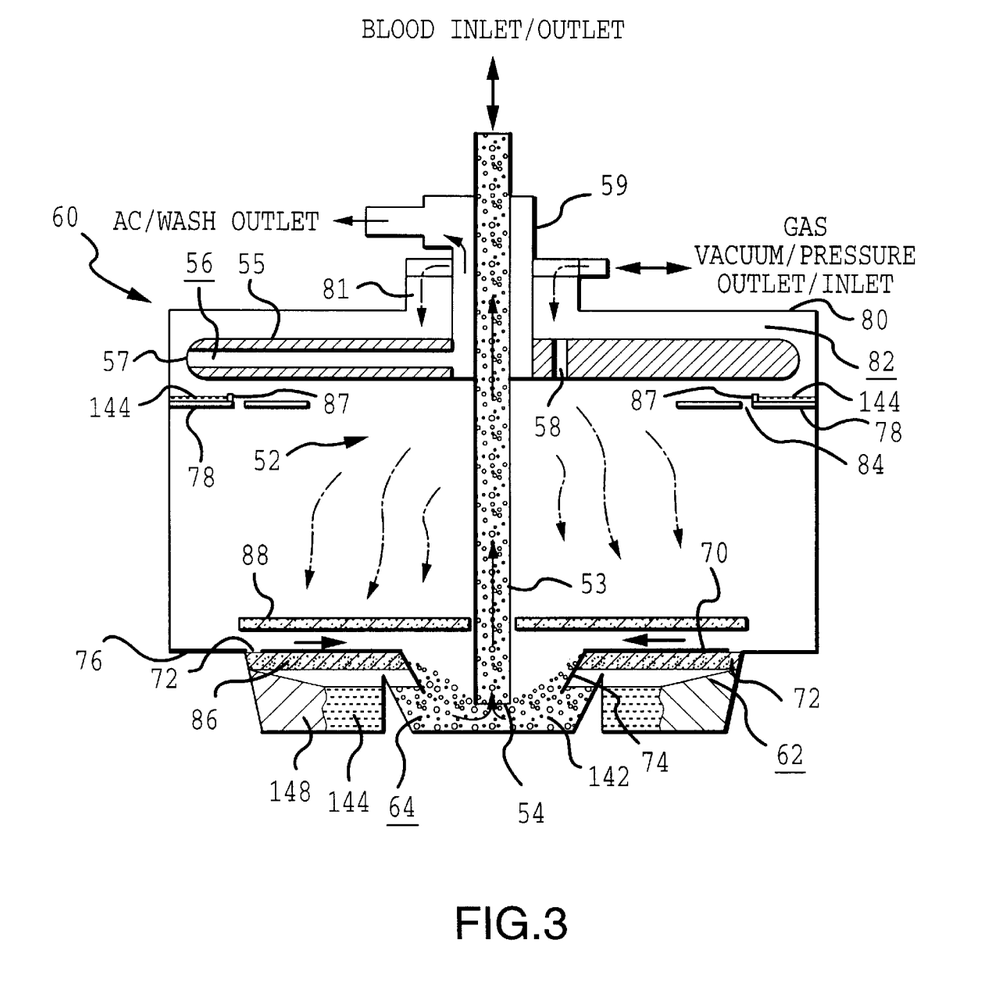
FIG. 3 is a cross-sectional side view of a containment bowl of the embodiment of FIG. 1 in a red blood cell removal mode, following blood processing (as illustrated in FIG. 2), wherein the separated/collected red blood cells are directed to the bottom of the bowl for removal and subsequent reinfusion.

As illustrated in FIGS. 2 and 3, the bottom of cylindrical bowl 60 includes an annular, cup-shaped region 62 for the collection and segregation of debris filtered from the blood, as will be discussed. The cup-shaped region 62 is defined by and segregated from an inner circular well region 64 by an upwardly and outwardly sloping inner wall 66 and adjoining vertical wall 68. To separate and direct fluid flow, a baffle plate 70 is interconnected in the containment bowl over the top of the annular, cup-shaped region 62 and includes a plurality of annularly-disposed holes 72 and a frusto-conical inner portion 74 disposed in parallel relation to the angled wall 66 to define a passage therebetween. Containment bowl 60 further includes an annular ledge wall 76 and an inwardly extending annular wall 78 defining a region therebetween for collecting and containing red blood cells during blood processing. The inwardly extending annular wall 78 is spaced from the ceiling wall 80 to define an upper region 82 in containment bowl 60. Inwardly extending annular wall 78 includes a plurality of annularly disposed holes 84 for receiving anticoagulant/wash solution into the upper region, and one or more upstanding ledges (or walls) 87 for containing residual anticoagulant/wash solution during removal of red blood cells from bowl 60, as will be further discussed.

The stator assembly 52 includes a central inlet/outlet tube 53 having a bottom end 54 positioned within said circular well region 64 of the containment bowl 60, and an annular fluid outlet disk 55 positioned within said upper region 82 of the containment bowl. Fluid outlet disk 55 is interconnected to an outlet tube 59 concentrically disposed about an upper portion of inlet/outlet tube 53. Fluid outlet disk 55 includes a plurality of radiating, or outwardly/inwardly extending passageways 56 each having an inlet port 57 at an outer edge of inlet disk 55. Additionally, the fluid inlet disk 55 includes an annular arrangement of vertical holes 58 therethrough (e.g., positioned between the radial passageways 56), for gas passage therethrough.

Containment bowl/stator assembly 50 also includes an annular filter 86 positioned immediately adjacent to below the ring of drain holes 72 and in contact with baffle plate 70 within the cup-shaped region 62. Such filter 86 filters debris from anticoagulated blood flowing into the bowl from tube 53 during blood processing. Such debris will be collected and segregated in the cup-shaped region 62. Filter 86 may, for example, comprise a polyester, woven screen with open pores having a maximum dimension of about $20\,\mu$–$60\,\mu$, and most preferably about $40\,\mu$ or less.

Containment bowl/stator assembly 50 may further include a defoamer element 88 positioned above baffle plate 70 for bursting gaseous bubbles within anticoagulated blood flowing into the bowl during processing. Defoamer element 88 may, for example, comprise a reticulated polyurethane sponge material having 30–70 pores per square inch and may be coated with an antifoam agent such as a mixture of dimethylpolysiloxane and silica gel. As will be appreciated, if the anticoagulant/wash solution to remove blood ratio is sufficiently high, a defoamer element may not be required.

As illustrated in FIG. 1, the bowl/stator assembly 50 may be supportably located in an upper chamber 122 of a housing assembly 120. For example, stator assembly 52 may be supportably suspended via a laterally pivotable arm module 124 and containment bowl 60 may be supportably positioned on rotatable plate 126. In turn, plate 126 may be connected to output shaft 93 of motor 92 for selective driven rotation. In this regard, both motor 92 and vacuum/pressurization pump 94 may be supportably located in a lower chamber 128 of housing assembly 120. Upper chamber 122 and lower chamber 128 are divided by a platform 130, wherein upper chamber 122 is adjusted to be readily accessible for interconnection/disconnection of the disposable bowl/stator assembly 50 and fluid transfer/storage assembly 20, and the operation of motor 92 and pump 94 is segregated. While FIG. 1 shows user interface/control assembly 100 as being separate from housing assembly 120 for illustration purposes, it will be appreciated that the user interface/control assembly 100 may be substantially housed in the housing assembly 120 to provide a physically integrated unit.

In this regard, a user interface/control module 110 may be provided for control over the operation vacuum/pressurization pump 94, motor 92 and clamps 40 and 42, via control lines 104, 107, and 106, respectively. More particularly, the user interface/control module 110 may be utilized to control the mode (i.e. vacuum v. pressurization) and timing start/stop of vacuum/pressurization pump 94, as well as the rate (e.g. RPMs of shaft 93) and timing start/stop of motor 92 via predetermined program(s)/input(s) and/or via selective user input instructions. The user interface/control module 110 may be further utilized to receive input from a sensor 112 via line 114, and to automatically suspend or terminate blood processing within bowl 60, and initiate the removal of red blood cells from bowl 60 as will be further described.

Figure 4A:
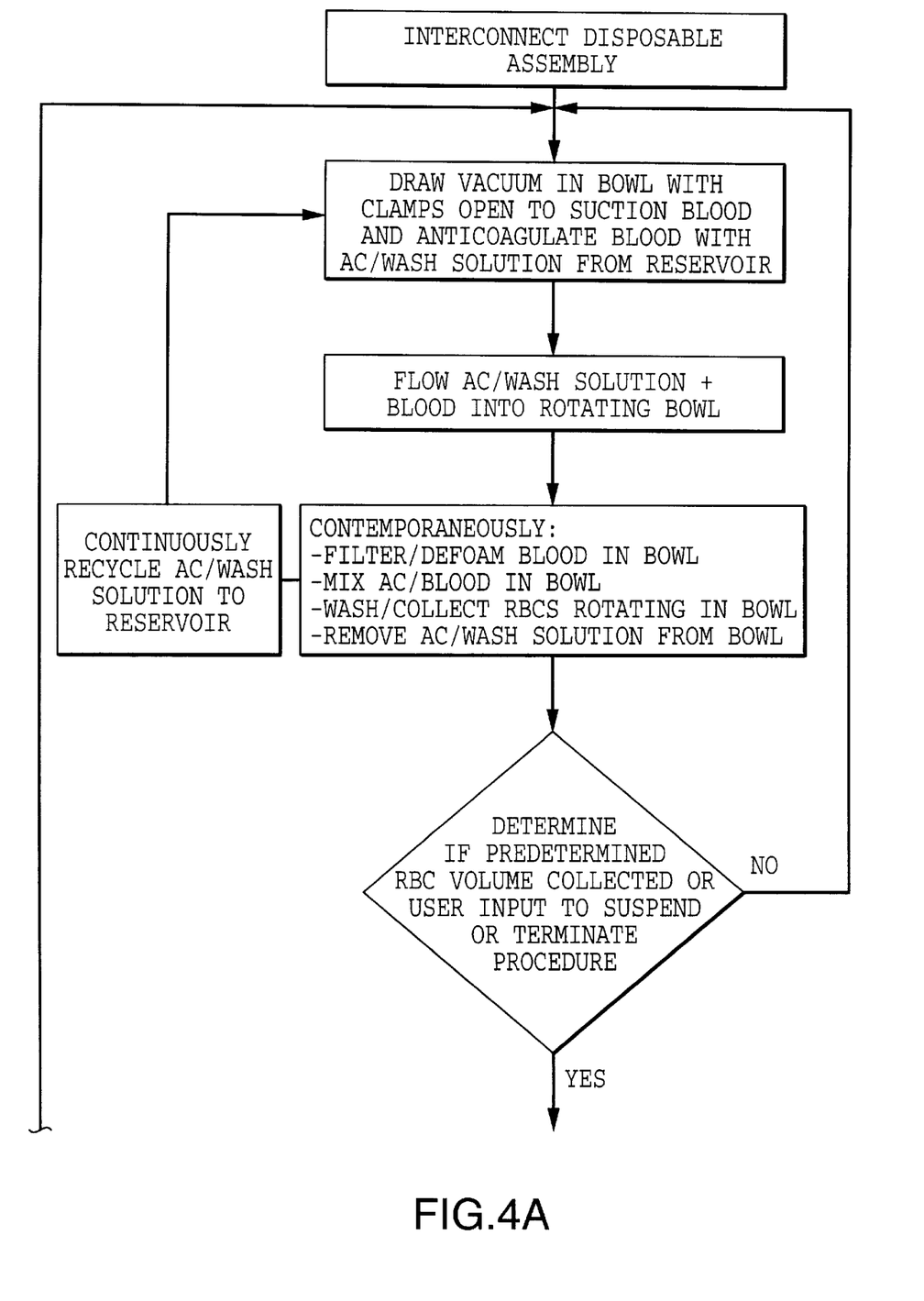
FIG. 4 is a process flow diagram corresponding with the embodiment of FIGS. 1–3.
Figure 4B:
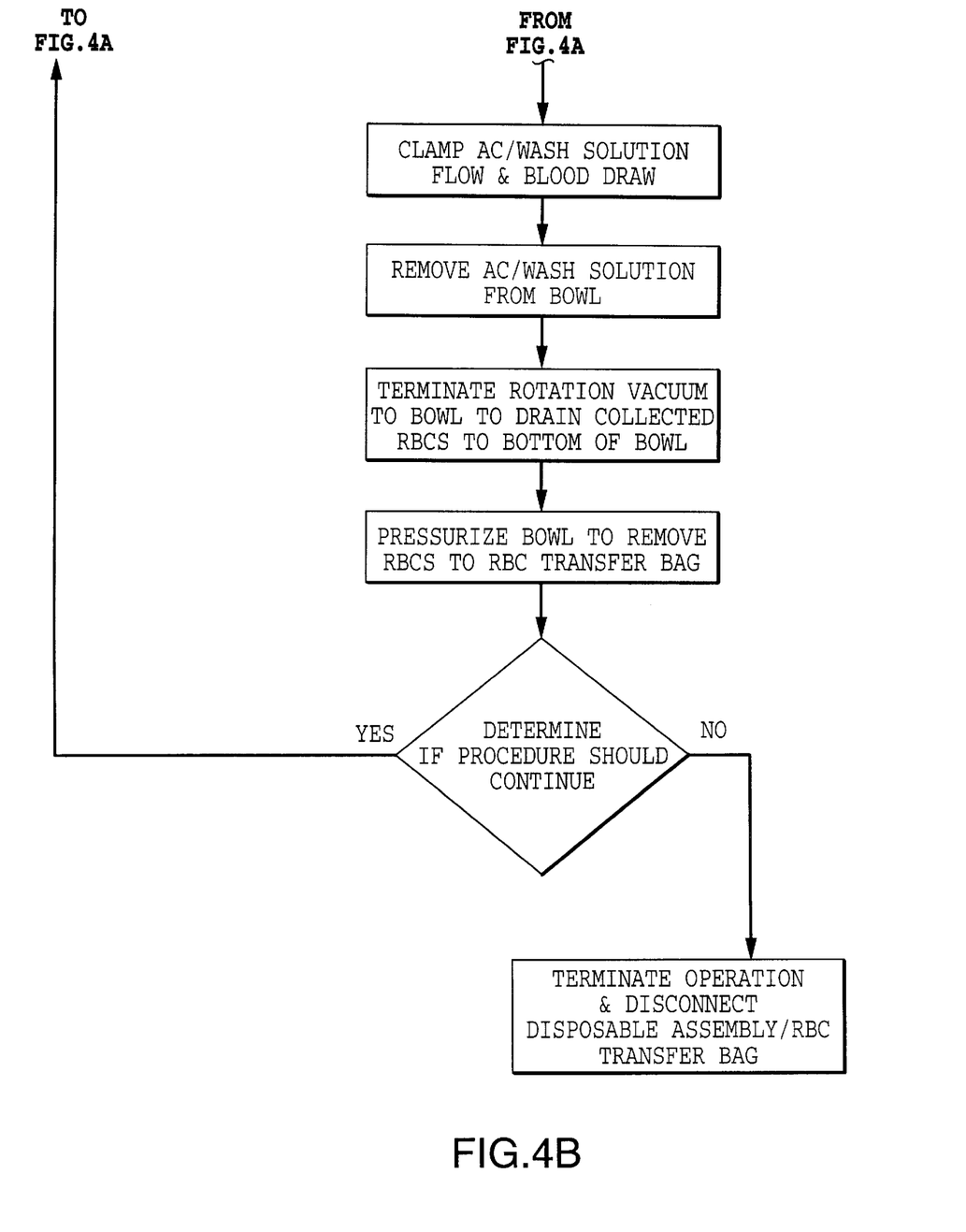

Referring now to FIGS. 4A and 4B in conjunction with FIGS. 1–3, operation of the illustrated embodiment will now be described. Initially, fluid transfer/reservoir assembly 20 and bowl/stator assembly 50, in the form of a disposable assembly, are removed from packaging and interconnected to system components for use. More particularly, bowl 60 is securely positioned on plate 126 for driven rotation by motor 92. Stator assembly 52 is interconnected to the stationary arm 124 included in housing assembly 52. A gas conduit 132, interconnected to vacuum/pressurization pump 97, is interconnected to bowl 60, for example via a rotatable seal member (e.g., positioned within arm module 124), so as to establish communication with annular gas port 81 provided at the top of bowl 60. Alternatively, gas conduit 132 may terminate immediately above platform 130 for selective vacuum/pressurization of the entire upper chamber 122 of housing assembly 120. In such an arrangement, a rotatable seal would not be necessary.

In further preparation for blood processing, anticoagulant/wash solution reservoir 24 is connected to a hanger support (not shown) that may be integrated with housing assembly 120 and located at an elevated position for gravity flow of anticoagulant/wash solution to suction device 22. The anticoagulant/wash solution may comprise, for example, a premixed ACD and saline wash solution in a ratio of about 1/5 to 1/10 by volume, and most preferably about 1/7 by volume. Transfer bag 34 may also be interconnected to a hanger support (not shown)/integrated with housing assembly 120.

To initiate blood processing, pump 94 draws a vacuum in the bowl 60 and transfer tubing line 28 so as to establish suction at suction device 22 for selective blood transfer by a user from the patient P. In this regard, it is noted that clamps 40 and 42 are both in an open position so as to permit anticoagulant/wash solution to flow from reservoir 24 through transfer line 26 and into transfer line 28, and to allow removed blood and anticoagulant solution to flow through transfer line 28 into the bottom of bowl 60 via the inlet/outlet tube 53 of the stator assembly 52. In conjunction with such anticoagulant/wash solution and blood flow, the motor 92 is initiated so as to rotate the containment bowl 60 about stator assembly 52.

As illustrated in FIG. 2, as anticoagulated blood flows out of the bottom 54 of inlet/outlet tube 53, it is spun from the circular well region 64 radially outward by the centrifugal force of rotating bowl 60 and directed upward by angled wall 66 into the cup-shaped region 62. Next, the anticoagulated blood is effectively forced through the filter 86 and passes through the holes 72 in baffle plate 70. The filtered debris and other contaminants 148 are spun to the outer wall of cup-shaped region 62, where they accumulate and pack-up (i.e. vertically and horizontally) thereby enhancing the operability of filter 86 by reducing any "coating over" of the surface of filter 86.

As the anticoagulated blood accumulates in the bowl 60, an annular fluid bed 140 will be established, and a centrifugal force pressure gradient will be created within the fluid bed 140. Such centrifugal force pressure gradient serves to separate the higher density red blood cells 142 from the anticoagulant/wash solution and other blood waste components, collectively 144, wherein the red blood cells 142 are further anticoagulated/washed by the anticoagulant/wash solution and collect in the region between annular ledge wall 76 and inwardly extending, annular wall 78 of the bowl 60. As illustrated, RBC-depleted fluid 144 will define an inner layer of fluid bed 140 and RBCs 142 will define an outer layer of fluid bed 140 during RBC collection.

The centrifugal force pressure gradient also serves to force gas entrained within the anticoagulated blood to the inner surface of the fluid bed 140 to form bubbles 146 and, upon contact with defoamer element 88, such bubbles are burst, and the gas is drawn through the defoamer element 88 and the vertical holes 58 for removal from the bowl through ports 81 and gas conduit 132 by vacuum pump 94.

As can be seen from FIG. 2, as the depth or surface of annular bed 140 rises (i.e progresses inward toward center axis AA), it will envelop the inlet ports 57 of the radiating passageways 56 of the outlet disk 55 of stator assembly 52. At such point, the centrifugal force pressure gradient will force the anticoagulant/wash solution and blood waste components, (collectively RBC-depleted fluid) 144 centripetally through radiating passageways 56 and vertically through outlet tube 59, through transfer tubing 36, and back into anticoagulant/wash solution reservoir 24 for re-use. In this regard, it is noted that, while not shown, fins or an open-cell element may be provided on, or immediately adjacent to, the ceiling wall 80 of bowl 60 to facilitate the generation of a sufficient centrifugal force pressure gradient so as to overcome the vacuum conditions and achieve fluid 144 removal during RBC collection.

As blood processing continues, the level of red blood cells 142 accumulated in the rotating bowl 60 may be monitored by sensor 112 to determine when a predetermined amount has been collected, whereupon further processing can be suspended or terminated. More particularly, for example, an optical sensor 112a may be positioned outside of the bowl 60 to transmit/receive pulsed radiation through the bowl 60 at a predetermined location, wherein a signal will be provided via line 114a when collected red blood cells have collected to the predetermined location. More particularly, the optical sensor 112a may transmit/receive pulsed infrared radiation (e.g. having a center-wavelength of about 940 nanometers through a correspondingly, optically transmissive region of bowl 60 (e.g. at least annular ledge wall 76), whereupon if the level of collected blood cells 142 has reached a predetermined level, a portion of the pulsed infrared radiation will be reflected back to and received by optical sensor 112a for generation of a signal to suspend blood processing. In an alternative arrangement, a fluid well 69 may be defined at a predetermined location of bowl 60, and will fill with red blood cells when a predetermined amount has been collected. Correspondingly, a sensor assembly 112b may be provided with a transmitter and receiver disposed on opposing sides of the fluid well 69 to sense when the well 69 is filled and provides a signal via line 114b.

When a predetermined amount of red blood cells has been collected, or should an operator otherwise selectively desire to suspend or terminate blood processing, clamps 40 and 42 are closed to stop the flow of anticoagulant/wash solution and anticoagulated blood through transfer lines 26 and 28, respectively. The driven rotation of bowl 60 by motor 92 is thereafter continued for a period sufficient to centripetally pump the RBC-depleted fluid (i.e., anticoagulant/wash solution and blood waste), collectively 144, within the bowl 60 to the point where such fluid no longer envelops the outlet ports 57 of outlet disk 55. In this regard, it should be noted that the annular arrangement of holes 84 through the inwardly extending wall 78 facilitate removal of the anticoagulant/wash solution via disk 55, so as to enhance anticoagulant recovery for re-use. Upon removal of the anticoagulant/wash solution, the operation of vacuum pump 94 and motor 92 may be suspended or terminated. Subsequently, the collected red blood cells 142 will flow down over the top of baffle plate 70 and the frusto-conical portion 74 into the center well region 64 of bowl 60. In this regard, it is noted that upstanding ledges 87 on inwardly projecting wall 78 not only provide for the collection of residual RBC-depleted fluid 144 for reuse, but also reduce flowback of the fluid 144 into the collected red blood cells 142. Operation of the pump 94 in a pressurization mode may be initiated to force the red blood cells 142 up through the fluid inlet/outlet tube 53. Since clamp 42 is closed, the red blood cells 142 will pass through transfer tubing 28 into tubing spur 30 and through the one-way check valve 32 into the transfer bag 34. As can be appreciated, due to the configuration of the bottom of the bowl 60, the collected red blood cells that are removed from the center well 64 are effectively segregated from the debris 148 collected in the outer annular, cup-shaped region 62. When the recoverable red blood cells 142 have been removed from the containment bowl 60, operation of pump 94 in the pressurization mode may be terminated, and operation of the pump 94 in a vacuum mode may be re-initiated together with the opening of clamps 40, 42 for continued blood processing. Alternatively, when the procedure is ultimately terminated, operation of motor 92 and pump 94 will not be reinitiated and the disposable assembly comprising the transfer tubing/storage assembly 20 and pump/stator assembly 50 may be disconnected. Of course, transfer bag 34 will be disconnected from such disposable assembly for reinfusion of the red blood cells to the patient P as may be desired in accordance with the given situation.

What is claimed is:

1. A method of autologous blood salvage comprising:
   introducing an anticoagulant into blood removed from a patient to yield a blood/anticoagulant mixture:
   flowing the blood/anticoagulant mixture into a containment area;
   rotating said containment area about a rotational axis to create a centrifugal force pressure gradient within the blood/anticoagulant mixture in the containment area;
   separating red blood cells from the accumulated blood/anticoagulant mixture within the containment area using said centrifugal force pressure gradient;
   cycling an anticoagulant-containing mixture from the containment area into a first reservoir for reuse in said introducing step; and
   filtering debris from said blood/anticoagulant mixture within said containment area.

2. A method of autologous blood salvage comprising:
   introducing an anticoagulant solution into blood removed from a patient to yield a blood/anticoagulant mixture wherein said anticoagulant solution comprises a wash fluid;
   flowing the blood/anticoagulant mixture into a containment area;
   rotating said containment area about a rotational axis to create a centrifugal force pressure gradient within the blood/anticoagulant mixture in the containment area;
   separating red blood cells from the accumulated blood/anticoagulant mixture within the containment area using said centrifugal force pressure gradient, said separating step including:
      employing centrifugal force resulting from said rotating step to force the blood/anticoagulant mixture through an annular filter;
      washing said red blood cells utilizing the wash fluid; and
   cycling an anticoagulant-containing mixture from the containment area into a first reservoir for reuse in said introducing step.

3. The method as recited in claim 2, wherein said annular filter has an average opening size of about 40 microns or less.

4. A method of autologous blood salvage comprising:
   applying a vacuum pressure to a containment area;
   utilizing said vacuum pressure to remove blood from a patient;
   introducing an anticoagulant into the blood removed to yield a blood/anticoagulant mixture;
   flowing the blood/anticoagulant mixture into a containment area;
   rotating said containment area about a rotational axis to create a centrifugal force pressure gradient within the blood/anticoagulant mixture in the containment area;
   separating red blood cells from the accumulated blood/anticoagulant mixture within the containment area using said centrifugal force pressure gradient;
   cycling an anticoagulant-containing mixture from the containment area into a first reservoir for reuse in said introducing step;
   separating gas bubbles contained in said blood/anticoagulant mixture within the containment area utilizing said centrifugal force pressure gradient;
   contacting said bubbles with a defoamer element in the containment area, wherein gas is released; and
   using said vacuum pressure to remove said released gas from said containment area.

5. A method of autologous blood salvage comprising:
   introducing an anticoagulant into blood removed from a patient;
   flowing at least partially anticoagulated blood into a containment area;
   filtering debris from anticoagulated blood within said containment area;
   rotating the containment area about a rotational axis to create a centrifugal force pressure gradient within anticoagulated blood accumulated in the containment area;
   separating red blood cells from filtered, anticoagulated blood using said centrifugal force pressure gradient.

6. A method as recited in claim 5, further comprising:
   segregating said debris within the containment area; and
   removing separated red blood cells from the containment area.

7. An apparatus for use in autologous blood salvage, comprising:
   a rotatable bowl defining a containment area, wherein said bowl includes a central bottom region, an outer, annular cup-shaped bottom region separate from said central bottom region, and an upstanding sidewall;
   a fluid conduit, positioned within the containment area, for introducing blood removed from a patient into said central bottom region; and,
   a filter positioned adjacently above said outer annular, cup-shaped bottom region, wherein upon rotation of said bowl said blood passes from said central bottom region into said outer, annular, cup-shaped bottom region and through said filter to remove one or more predetermined components therefrom and segregate said one or more predetermined components in said outer, annular, cup-shaped bottom region.

8. An apparatus as recited in claim 7, further comprising:
   a baffle plate positioned substantially completely over said filter and cup-shaped bottom region, and having one or more openings positioned adjacent to the filter for passage of filtered blood therethrough.

9. An apparatus as recited in claim 7, wherein a centrifugal force pressure gradient is generated in a fluid bed of filtered blood accumulating during use, and wherein said fluid bed includes an outer layer of red blood cells and inner layer of red blood cell-depleted fluid.

10. An apparatus as recited in claim 9, further comprising:
    a defoamer element, positioned within said containment area, for contacting gas bubbles accumulating at an inner surface of said fluid bed during use.

11. An apparatus as recited in claim 9, further comprising:

a second conduit, positioned within said containment area and extending towards a central, longitudinal axis, of said bowl for removing said depleted fluid from said fluid bed accumulating during use, wherein said centrifugal force pressure gradient pumps said red blood cell depleted fluid centripetally through said second conduit and out of said containment area.

12. An apparatus as recited in claim 11, said bowl including a wall projecting inwardly from said sidewall, wherein said second conduit is positioned above said inwardly projecting wall, and wherein said layer of accumulated red blood cells are contained below said inwardly projecting wall during use.

13. An apparatus as recited in claim 12, wherein said inwardly projecting wall includes a plurality of openings therethrough.

14. An apparatus as recited in claim 13, wherein said inwardly projecting wall includes at least one upstanding ledge to define a fluid collection region above said inwardly projecting wall.

15. An apparatus as recited in claim 11, wherein said second conduit includes a disk-shaped member having a plurality of radiating passageways.

16. An apparatus as recited in claim 15, wherein said disk-shaped member includes one or more upwardly disposed passageways for the passage of gas therethrough for removal from said containment area during use.

17. An apparatus as recited in claim 7, wherein said cup-shaped bottom region and said filter are of an annular configuration.

18. An apparatus as recited in claim 17, wherein said filter includes pores having a maximum dimension of about 40 microns or less.

19. A method as recited in claim 5, wherein said containment area is defined by a bowl having a central bottom region, an outer cup-shaped bottom region separate from said central bottom region and an upstanding wall, and wherein said filtering step comprises:

passing said anticoagulated blood from said central bottom region into said outer cup-shaped bottom region and through a filter positioned over at least a portion of said outer cup-shaped bottom region.

20. A method as recited in claim 19, wherein a baffle plate is positioned substantially completely over said filter and cup-shaped bottom region, and includes one or more openings positioned adjacent to the filter for passage of filtered anticoagulated blood therethrough.

21. A method as recited in claim 5, wherein during said rotating step filtered, anticoagulated blood accumulates in a fluid bed in said containment area, and wherein said method further comprises:

contacting gas bubbles accumulating at an inner surface of said fluid bed with a defoamer element.

22. A method as recited in claim 5, wherein during said rotating step a fluid bed of anticoagulated, filtered blood accumulates in said containment area, said fluid bed including an outer layer of said red blood cells and an inner layer of red blood cell-depleted fluid, and wherein said method further comprises:

utilizing said centrifugal force pressure gradient to pump said red blood cell-depleted fluid centripetally through a conduit positioned within said containment area and toward said rotational axis, and then out of said containment area.

23. A method as recited in claim 22, wherein said containment area is defined by a bowl having a wall projecting inwardly from a sidewall of the bowl, wherein said conduit is positioned above said inwardly projecting wall, and wherein said red blood cells are contained below said inwardly projecting wall during said rotating step.

24. A method as recited in claim 23, wherein said inwardly projecting wall includes a plurality of openings therethrough.

25. A method as recited in claim 22, wherein said conduit includes a laterally-disposed disk-shaped member having a plurality of radiating passageways.

26. A method as recited in claim 25, wherein said disk-shaped member includes one or more upwardly disposed passageways therethrough for the passage of gas out of said containment area during use.

* * * * *